United States Patent [19]

Stephan et al.

[11] 4,170,590

[45] Oct. 9, 1979

[54] ION EXCHANGER TREATMENT OF CITRATE-STABILIZED PLASMA

[75] Inventors: Wolfgang Stephan, Dreieichenhain; Ronald Kotitschke, Dreieich, both of Fed. Rep. of Germany

[73] Assignee: Biotest-Serum-Institut GmbH, Frankfurt am Main, Fed. Rep. of Germany

[21] Appl. No.: 875,489

[22] Filed: Feb. 6, 1978

Related U.S. Application Data

[63] Continuation-in-part of Ser. No. 639,960, Dec. 11, 1975, Pat. No. 4,081,431.

[30] Foreign Application Priority Data

Dec. 14, 1974 [DE] Fed. Rep. of Germany ....... 2459291

[51] Int. Cl.$^2$ ............................................... A23J 1/06
[52] U.S. Cl. ................................... 260/112 B; 424/101
[58] Field of Search ...................... 260/112 B; 424/101

[56] References Cited

U.S. PATENT DOCUMENTS

| | | | |
|---|---|---|---|
| 3,652,530 | 3/1972 | Johnson et al. | 260/112 B |
| 3,682,881 | 8/1972 | Fekete et al. | 260/112 B |
| 3,869,436 | 3/1975 | Falksveden | 260/112 B |
| 3,916,026 | 10/1975 | Stephan | 424/177 |
| 3,920,625 | 11/1975 | Andersson et al. | 260/112 B |
| 3,973,002 | 8/1976 | Hagan et al. | 260/112 B X |

OTHER PUBLICATIONS

Laursen et al., *Chemical Abstracts*, vol. 67:50,325p (1967).
Reid et al., *Ind. & Eng. Chem.*, vol. 43, No. 5 (1951), pp. 1074 and 1075.
Tullis et al., *The New England Journal of Medicine*, vol. 273, No. 13 (1965), pp. 667–674.

*Primary Examiner*—Walter C. Danison
*Attorney, Agent, or Firm*—Sprung, Felfe, Horn, Lynch & Kramer

[57] ABSTRACT

A citrate-stabilized blood plasma is frozen and thawed, the undissolved cryoprecipitate is separated and is rich in factor VIII protein. The residual liquid is treated with cation and anion exchangers, either sequentially or in admixture, to separate calcium and citrate ions therefrom. The residual plasma is then subjected to adsorption to remove a fraction which is eluted and precipitated, enriched in factors II, VII, IX and X. The liquid left from adsorption is subjected to further adsorption with silicic acid, leaving a storage-stable serum. The silicic acid is eluted to dissolve adsorbed fibrinogen which then is re-precipitated.

7 Claims, 1 Drawing Figure

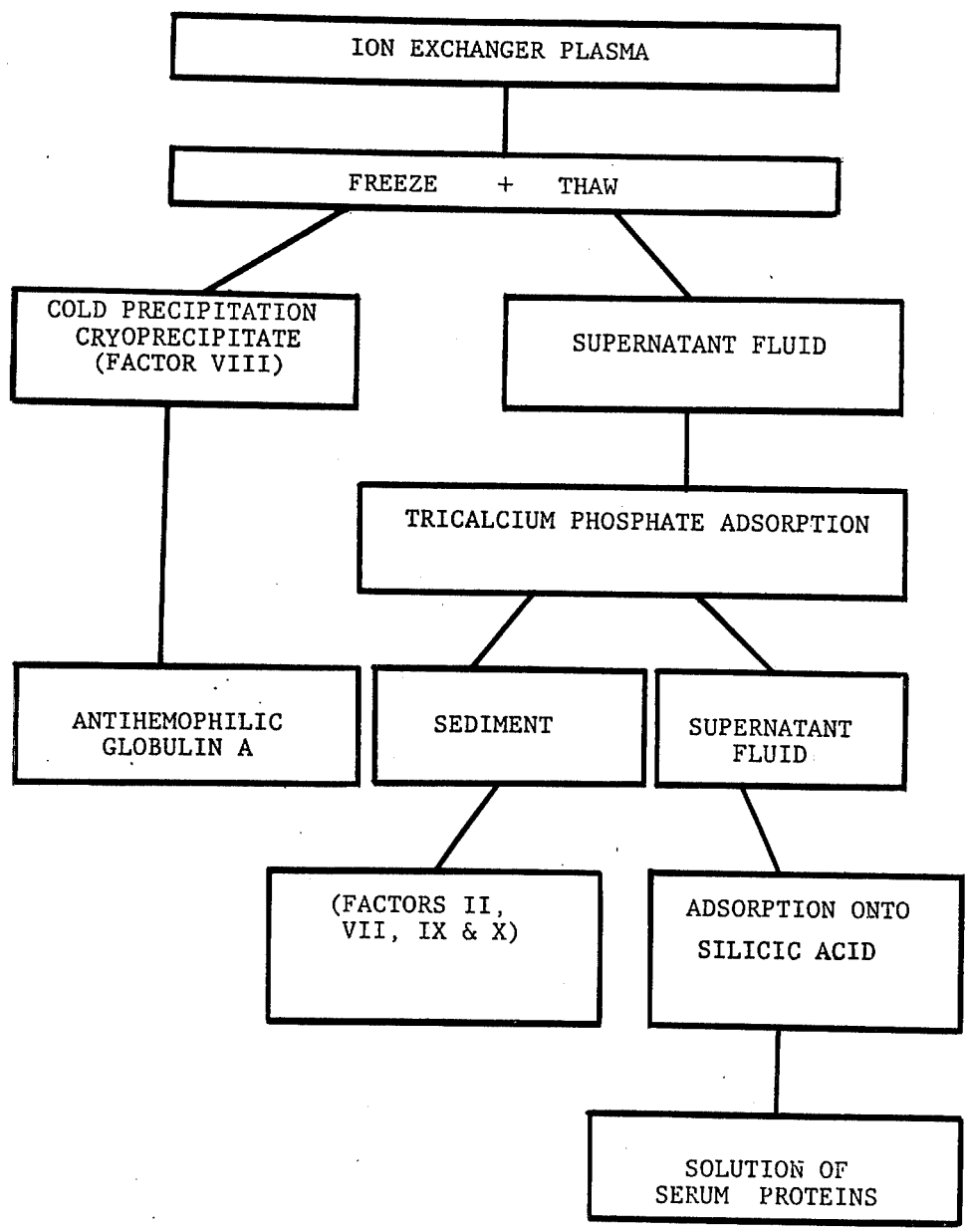

ION EXCHANGER TREATMENT OF CITRATE-STABILIZED PLASMA

This application is a continuation-in-part of Application Ser. No. 639,960, filed Dec. 11, 1975, now U.S. Pat. No. 4,081,431.

This application relates to a process for preparing various blood fractions from citrate plasma.

In application Ser. No. 639,960, filed Dec. 11, 1975 there is described a process for the fractionation of blood starting with ion exchange. That process involved treating blood from a donor with a cation exchanger, separating the solids from the plasma, freezing the plasma, thawing the frozen plasma and separating from the thawed plasma fluid a first product comprising undissolved cryoprecipitate enriched in factor-VIII protein; dissolving the first product, removing impurities from the solution of the first product, precipitating the factor-VIII protein from the solution; after separation of the first product treating the residual thawed plasma fluid with a solid adsorbent thereby to adsorb the factors II, VII, IX and X, and separating a second product comprising solid adsorbent and the adsorbed factors from the residual plasma; and, after separation of the second product, contacting the residual plasma with colloidal silica and separating a third product comprising a storage-stable serum protein solution from the colloidal silica.

Since much blood is promptly mixed with citrate as a stablizer, however, such blood was not directly suitable for use in such process. Specifically, if blood is removed in citrate-containing stabilizers, then the coagulation of the blood is prevented by complex binding of the blood calcium with citrate since, as is known, free $Ca^{++}$-ions must be present for coagulation. Therefore $Ca^{++}$ is one of the coagulation factors, designated as coagulation factor IV. By ion exchanger treatment of citrate-stabilized plasma the citrate can be taken up by the ion exchanger whereby $Ca^{++}$-ions are liberated and are again available for coagulation.

Since the blood fractionation procedure of our earlier application referred to hereinabove is not directly applicable to citrate-stabilized plasmas, it is an object of the present invention to expand and/or modify that fractionation process to permit its general use on citrate-stabilized plasma as well.

This object has been realized in accordance with the present invention pursuant to which it has been found that modification of the ion exchange treatment of our earlier application with respect to type and stage in the process will permit the desired fractionation to proceed.

In accordance with another aspect of the invention it has been found that the fractionation may be carried further to obtain an additional product.

$Ca^{++}$ ions of residual plasma stabilized with citrate can be exchanged by treatment with a cation exchanger on the $Na^+$ or $H^+$ cycle. If subsequent to this exchange the citrate-containing plasma is treated with an ion exchanger having $Cl^-$- or $OH^-$-ions, then the effect of the stabilization will be the same as is realized when $Ca^{++}$ is removed from blood, directly during taking of blood, with a cation exchanger and exchanged $H^+$ or $Na^+$ ions. The exchange of the $Ca^{++}$ ions and citrate ions of a citrate plasma can also take place in a single step by use of a mixed bed (of cation and anion exchanger particles). This exchange of the $Ca^{++}$ and citrate ions for $H^+$ and $OH^-$ ions (or $Na^+$ and $Cl^-$ ions) make it possible to produce an ion exchanger plasma from a citrate plasma. Such treatment is desirably practiced at a particular stage of the process.

The citrate-stabilized plasma, obtained by separating the solids from blood either before or after citrate-stabilization, is treated to remove a factor VIII containing cryoprecipitate.

Preferably, the citrate plasma used is frozen at about −40° C. within about 48 hours after taking the blood from a donor. This serves to retain the factor VIII activity. The obtaining of a cryoprecipitate from this citrate plasma takes place in the manner described in our earlier application, viz, thawing and filtration. The citrate plasma freed of cryoprecipitate is treated even at room temperature by a cation exchanger, e.g., polystyrene-sulfonate-cation exchanger, and an ion exchanger, e.g., -polystyrene-divinyl benzene/quaternary amine, it being possible for the conversion of the citrate plasma to ion exchanger plasma to be effected batchwise or continuously in a column.

By the cation exchanger treatment $Ca^{++}$ in the citrate plasma is exchanged for $Na^+$ or $H^+$ ions. The anion exchanger exchanges the citrate ions of the citrate plasma for $OH^-$ or $Cl^-$ ions. The exchange of the $Ca^{++}$ ions and citrate ions of the citrate plasma can either take place successively or simultaneously in a mixed bed.

The ion exchanger plasma prepared in this manner is now suited for the recovery of a prothrombin complex concentrate and storage-stable serum proteins by the procedures of our earlier application. As there, colloidal silicic acid, which preferably has a specific surface of about 50–400 $m^2$ per gram and which adsorbs coagulation factors and other unstable proteins still in the plasma, is a suitable starting material for obtaining fibrinogen. The fibrinogen is adsorbed by the colloidal silicic acid and can be liberated therefrom by common salt, preferably in the form of an about 10% solution. By dialysis and ultrafiltration of the eluate, a sterile filterable fibrinogen solution results. The fibrinogen can be stabilized by freeze drying and, after solution with sterile water, is suitable for therapeutic use.

The accompanying drawing is a flow sheet of the process commencing with citrate-stabilized plasma, converting it along the way to an ion exchanger plasma, and ending up with various blood fractions.

The process of the invention is described in greater detail in the following illustrative examples wherein all parts are by weight unless otherwise expressed:

EXAMPLE 1

Preparation of ion exchanger plasma from citrate plasma

Nine parts of venous blood from donors were added to one part of a 3.8% sodium citrate stabilizer solution. The blood was centrifuged shortly after it had been taken and the erythrocytes, after suspension in physiological saline solution, were reinfused into the donor. The plasma was frozen at −40° C. less than 48 hours after collection.

The frozen plasma was thawed at +4° C. It was centrifuged and the cold cryoprecipitate was dissolved in the warm (room temperature, not over 30° C.) with tris buffer. Then the solution was cleared by centrifugation and/or filtration of undissolved protein components. The dissolved cryoprecipitate was stirred at room temperature with Al(OH)$_3$ gel. After the removal of the adsorbent, the remaining liquid was treated by the addition of 0.5 M trisodium citrate solution (the sodium citrate can also be added in solid form or in other concentrations) to make it an 0.02 M trisodium citrate solution, and adjusted to a pH of 6.1 with 0.02 M citric acid (the citric acid can also be added in solid form or in other concentrations, the pH of 6.1 being the optimum value, although it can be higher or lower, so that the result is a pH range from 5.7 to 7.8). Then polyethylene glycol having an average molecular weight of 4000 was added in solid form to the solution in such an amount that its concentration amounted to a maximum of 5%, and preferably to 3%. After the centrifugation that followed, the sediment was discarded. Colloidal silica was added to the supernatant liquid up to a concentration not greater than 5% and preferably 3% by weight. Especially good results were obtained if the mixture was gently stirred for 2 hours at room temperature. Then it was centrifuged. By increasing the concentration of the polyethylene glycol in the supernatant fluid to no more than 12%, and preferably 10%, the antihemophilic globulin A was precipitated and then removed by centrifugation.

The precipitate was washed with cold (e.g., 2° C.) buffered washing water, the washing buffer was then decanted, and the sediment was dissolved by gentle stirring in a small amount of factor VIII solution buffer medium, amounting, for example, to 1/100 of the initial volume of the plasma. The solution was then irradiated with ultraviolet light in a revolving continuous-flow apparatus (Dill apparatus). The radiation intensity amounted to a maximum of 2 mW per minute per square centimeter at a wavelength of 254 nm, and preferably to 1 mW per minute. The irradiation solution was sterile-filtered in a known manner. The protein solution thus obtained contains an antihemophilic globulin concentrate of high effectiveness, and can be freeze-dried without loss of activity. If it is dissolved in half of the decanted volume with water, it contains ten to twenty times the factor VIII activity of a normal plasma, in a protein concentration containing only a twentieth of the amount of protein contained in plasma of the same content of antihemophilic globulin activity. The concentrate can be administered intravenously to patents suffering from a deficiency of factor VIII activity (hemophilia).

The supernatant plasma from the centrifugation of the thawed material was used for the production of a prothrombin complex concentrate of fibrinogen and a solution of stable serum proteins.

The following reagents were used for the further processing:

(1) cation exchanger: polystyrene-sulfonate cation exchanger in the Na+ or H+ form.

(2) Ion exchanger: polystyrene/divinyl benzene/-quaternary amine in the Cl− or OH−form.

According to the resin producer's specification, the exchangers were either brought into the Na+ and Cl− or H+ and OH− form, the resins being used during the conversion of the citrate plasma into an ion exchanger plasma in the mixed bed process in the H+ or OH− form and in the case of sequential exchanges in the Na+ or Cl− form. The adsorption can take place batchwise or continuously in columns.

EXAMPLE 2

(a) Batch Process 75 ml of ion exchanger were added to 1 liter of plasma and the resin plus adsorbed material was centrifuged off from the plasma. The resin was regenerated and the process twice repeated. The citrate concentration of the adsorbed plasma was determined. The results are given in Table I.

(b) Columnar Process

A chromatography tube was filled with 75 ml of ion exchanger resin. 1 liter of citrate plasma was passed through the column. 100 ml fractions were collected and the citrate concentration of the fractions was determined. These results are also given in Table I.

Table I

| Comparison of batch and columnar ion exchange processes | | | |
|---|---|---|---|
| Batch process | | Citrate in liquid, mg/l | Columnar process |
| Start (citrate plasma) | 48.8 | Start | 48.8 |
| Adsorption 1 | 24.5 | Fraction 1 | 0.15 |
| 2 | 11.9 | 2 | 0.37 |
| 3 | 4.4 | 3 | 1.29 |
| | | 4 | 3.01 |
| | | 5 | 6.28 |
| | | 6 | 13.7 |
| | | 7 | 30.6 |

Production of Prothtombin Complex Concentrate and Stable Proteins

The ion exchanger plasma obtained from citrate plasma by the use of ion exchangers is just as suitable for the preparation of prothrombin complex concentrate and storage-stable serum proteins as ion exchanger plasma obtained directly from unstabilized blood.

EXAMPLE 3

The prothrombin complex, also referred to as PPSB, contains the following:
P=prothrombin factor (factor II)
P=proconvertin (factor VII)
S=Stuart-Prower factor (factor X), and
B=antihemophilic globulin B (factor IX).

Reagents

Caustic soda solution: 1N NaOH solution
$\beta$-propiolactone: freshly distilled $\beta$-propiolactone.
Tricalcium phosphate: The preparations of a number of manufacturers are suitable (Merck, Reiden de Haen and others).
Citrate solution: 0.05 M trisodium citrate solution.
Acetic acid: 2N acetic acid solution.

Procedure:

$\beta$-Propiolactone was added at room temperature to ion exchanger plasma from which the cryoprecipitate had been removed by the method described above, until a concentration of 0.05% to a maximum of 0.3%, preferably a concentration of 0.25%, was reached. The mixture was stirred for one hour at room temperature, and during this period the pH value was maintained at levels between 6.5 and 8.0, preferably at 7.2, by the continuous addition of NaOH. After ultraviolet irradiation in a Dill apparatus, the hydrolysis of the $\beta$-propiolactone was continued to completion by the continuous addition of NaOH while maintaining the pH constant, until the pH remained constant without the further addition of NaOH. The ion exchanger plasma treated with β-propiolactone and irradiated was then adsorbed with tricalcium phosphate at room temperature to a concentration of 0.8 wt.-%, preferably with exchanger eluate from Example 2 until a concentration of 0.25% was reached. The mixture was stirred for one hour at room temperature, and during this period the pH value was maintained at levels between 6.5 and 8.0, preferably at 7.2, by the continuous addition of NaOH. After ultraviolet irradiation in a Dill apparatus, the hydrolysis of the β-propiolactone was continued to completion by the continuous addition of NaOH while maintaining the pH constant, until the pH remained constant without the further addition of NaOH. The ion exchanger plasma treated with β-propiolactone and irradiated was then adsorbed with tricalcium phosphate at room temperature to a concentration of 0.8 wt.-%, preferably with at least 0.1 wt.-% thereof. Greater amounts of tricalcium phosphate can be used, or repeated treatment therewith can be performed, but this offers no advantages. Then the mixture was centrifuged and the sediment was further processed to obtain PPSB concentrate, while the supernatant liquid served as a starting material for the preparation of the third product of the process. The sediment was eluted with a citrate solution, and the combined eluates were treated with colloidal silica to a concentration of no more than 3 wt.-%, and preferably of 0.5 wt.-%. After adsorption and removal of the silica precipitate, the pH of the supernatant fluid was adjusted with acetic acid to 6.8. It was found advantageous then to concentrate the solution in an ultrafiltration apparatus to about ⅓ to 1/5 of its volume, then subject it to sterile filtration and freeze-drying.

If the freeze-dried PPSB concentrate is dissolved in water, it contains about 25 times the PPSB factor activity of a normal plasma. The concentrate is suitable for the treatment of deficiency diseases such as hemophilia B.

Preparation of the Solution of Stable Proteins (third product of the process)

Ion exchanger plasma treated as in the two process steps described above was adsorbed with colloidal silica to a concentration of 3 wt.-%, centrifuged and filtered sterile. 1 to 5 wt.-% of silica can also be used.

Preparation of Fibrinogen

After separation of the colloidal silicic acid, it was washed twice with 500 ml of 0.9% NaCl containing 60 mg/l of citrate. The colloidal silicic acid which was centrifuged off was then twice extracted with 400 ml of a 10% NaCl solution containing 60 mg/l of citrate, for one hour at room temperature. Alcohol was added to the combined eluates to form a precipitate of fibrinogen which was dissolved in citrate-containing physiological NaCl solution, sterile filtered and freeze dried. Table II presents the results of such procedure:

Table II

| | Preparation of fibrinogen | | | |
|---|---|---|---|---|
| | Volume ml | Protein g % | Fibrinogen mg | Yield % |
| Starting plasma | 1,000 | 6.5 | 235 | 100 |
| Eluate 1 | 400 | 0.66 | 140 | } 54 |

Table II-continued

| | Preparation of fibrinogen | | | |
|---|---|---|---|---|
| | Volume ml | Protein g % | Fibrinogen mg | Yield % |
| Eluate 2 | 400 | 0.47 | 200 | |

EXAMPLE 4

250 ml of cation exchanger (in the H+ form) and 375 ml of anion exchanger (in the OH− form) were mixed and put into a chromatography tube. 1.45 liters of supernatant citrate plasma from Example 1 were poured through the resin mixture. Table III shows the results.

Table III

| Ion Concentration, Mixed Bed Process | | | | |
|---|---|---|---|---|
| | Ion concentration in mg/l | | | |
| | Citrate | Calcium | Sodium | Chloride |
| Starting plasma | 66.1 | 4.15 | 216 | 83 |
| After exchange | 1.74 | 0 | 84 | 59 |

The ratio of anion to cation exchanger can be varied. In practice about 1:1.5 cation to anion by volume has proved quite satisfactory. The resins can also be used in the Na+ or Cl− form, which merely leads to a somewhat higher concentration of sodium and/or chloride ions.

EXAMPLE 5

120 ml of cation exchanger in the Na+ form were placed into a chromatography tube. 1 liter of citrate plasma as in Example 4 was poured through a second chromatography tube containing 180 ml of anion exchanger in the Cl−-form. Table IV shows the results of these trials:

Table IV

| Ion Concentration - Sequential Exchange | | |
|---|---|---|
| | Ion concentration in mg/l | |
| | Citrate | Calcium |
| Starting plasma | 64.0 | 4.10 |
| After cation exchange | 63.0 | 0.60 |
| After anion exchange | 0.49 | 0.60 |

The exchangers can also be present in the H+ plus Na+ form or OH− plus Cl− form.

It will be appreciated that the instant specification and examples are set forth by way of illustration and not limitation and that various modifications and changes may be made without departing from the spirit and scope of the present invention.

What is claimed is:

1. In the fractionation of blood comprising the steps of taking blood from a donor, separating the solids from the plasma, freezing the plasma, thawing the frozen plasma and separating from the thawed plasma fluid a first product comprising undissolved cryoprecipitate enriched in factor-VIII protein; dissolving the first product, removing impurities from the solution of the first product, precipitating the factor-VIII protein from the solution; after separation of the first product treating the residual thawed plasma fluid with a solid adsorbent thereby to adsorb the factors II, VII, IX and X, and separating a second product comprising solid adsorbent and the adsorbed factors from the residual plasma; and, after separation of the second product, contacting the residual plasma with colloidal silica and separating a third product comprising a storage-stable serum protein solution from the colloidal silica, the improvement which comprises mixing the blood or plasma with a citrate stabilizer prior to freezing and treating the residual thawed plasma fluid with an anion exchange resin and a cation exchange resin prior to treatment with the solid adsorbent.

2. A process according to claim 1, including the further steps of extracting the colloidal silica separated from the storage-stable serum protein solution with a solvent solution to dissolve fibrinogen, and then adding to said solution a precipitant for fibrinogen.

3. A process according to claim 1, wherein the anion and cation exchangers are mixed together.

4. A process according to claim 1, wherein the anion and cation exchangers successively contact the plasma.

5. A process according to claim 1, wherein the cation exchanger is initially in the sodium or hydrogen form.

6. A process according to claim 1, wherein the anion exchanger is initially in the chloride or hydroxide form.

7. A process according to claim 2, wherein the cation exchanger is initially in the sodium or hydrogen form, and the anion exchanger is initially in the chloride or hydroxide form.

* * * * *